US010827911B2

(12) United States Patent
Ramachandran et al.

(10) Patent No.: US 10,827,911 B2
(45) Date of Patent: Nov. 10, 2020

(54) OPTICAL IMAGING SYSTEM EMPLOYING VORTEX FIBER FOR MULTIPLE-MODE ILLUMINATION

(71) Applicants: Trustees of Boston University, Boston, MA (US); OFS FITEL, LLC, Norcross, GA (US)

(72) Inventors: Siddharth Ramachandran, Boston, MA (US); Lu Yan, Sunnyvale, CA (US); Poul Kristensen, Valby (DK)

(73) Assignees: Trustees of Boston University, Boston, MA (US); OFS FITEL, LLC, Norcross, GA (US)

( * ) Notice: Subject to any disclaimer, the term of this patent is extended or adjusted under 35 U.S.C. 154(b) by 0 days.

(21) Appl. No.: 16/306,026

(22) PCT Filed: Jun. 5, 2017

(86) PCT No.: PCT/US2017/035936
§ 371 (c)(1),
(2) Date: Nov. 30, 2018

(87) PCT Pub. No.: WO2017/210679
PCT Pub. Date: Dec. 7, 2017

(65) Prior Publication Data
US 2019/0290100 A1    Sep. 26, 2019

Related U.S. Application Data

(60) Provisional application No. 62/345,022, filed on Jun. 3, 2016.

(51) Int. Cl.
*A61B 1/00* (2006.01)
*F21V 8/00* (2006.01)
(Continued)

(52) U.S. Cl.
CPC .......... *A61B 1/0017* (2013.01); *G02B 6/0008* (2013.01); *G02B 6/02071* (2013.01);
(Continued)

(58) Field of Classification Search
CPC ................................... A61B 1/0017
See application file for complete search history.

(56) References Cited

U.S. PATENT DOCUMENTS 5,499,134 A    3/1996   Galvanauskas et al.
6,295,395 B1   9/2001   Paek
(Continued)

OTHER PUBLICATIONS

Siddharth Ramachandran and Poul Kristensen, "Optical vortices in fiber", 2013 Science Wise Publishing & De Gruyter, Nanophotonics 2013; 2(5-6): pp. 455-474.
(Continued)

*Primary Examiner* — Rhonda S Peace
(74) *Attorney, Agent, or Firm* — BainwoodHuang (57) ABSTRACT

A vortex optical fiber for use in an illumination subsystem of an optical imaging system (e.g., a stimulated emission depletion (STED) microscopy system) includes an elongated optically transmissive medium having a set of regions including a core region, a trench region surrounding the core region, a ring region surrounding the trench region, and a cladding region, the set of regions having a doping profile providing a $\Delta n_{\it eff}$ for vector modes in an $LP_{11}$ mode group of greater than $1 \times 10^{-4}$ in the visible spectral range so as to simultaneously guide stable Gaussian and orbital angular momentum (OAM) carrying modes at corresponding visible wavelengths.

46 Claims, 10 Drawing Sheets

(51) Int. Cl.
G02B 6/02 (2006.01)
G02B 21/00 (2006.01)
G02B 6/036 (2006.01)
H01S 3/094 (2006.01)
G02B 6/028 (2006.01)
G02B 27/58 (2006.01)

(52) U.S. Cl.
CPC ..... G02B 6/02195 (2013.01); G02B 6/02366 (2013.01); G02B 6/02395 (2013.01); G02B 6/03644 (2013.01); G02B 21/0028 (2013.01); G02B 21/0032 (2013.01); G02B 21/0076 (2013.01); H01S 3/094 (2013.01); *G02B 6/0286* (2013.01); *G02B 27/58* (2013.01)

(56) References Cited

U.S. PATENT DOCUMENTS

| | | | |
|---|---|---|---|
| 7,177,510 B2 | 2/2007 | Ramachandran | |
| 8,031,924 B2* | 10/2011 | Can | G01N 21/6428 382/128 |
| 8,686,363 B1 | 4/2014 | Timlin et al. | |
| 9,170,367 B2* | 10/2015 | Messerly | G02B 6/02 |
| 9,270,080 B1 | 2/2016 | Clowes et al. | |
| 10,261,244 B2* | 4/2019 | Ashrafi | G02B 6/02342 |
| 2012/0159995 A1 | 6/2012 | Borel et al. | |
| 2015/0104139 A1 | 4/2015 | Brunet et al. | |
| 2016/0127073 A1 | 5/2016 | Ashrafi et al. | |
| 2017/0280211 A1* | 9/2017 | Damaghi | H04B 10/118 |
| 2017/0343791 A1* | 11/2017 | Swanson | G02B 23/2469 |
| 2019/0290100 A1* | 9/2019 | Ramachandran | G02B 6/02195 |

OTHER PUBLICATIONS

Lu Yan, et al., "Modal-Weight Measurements With Fiber Gratings", Journal of Lightwave Technology, vol. 33, No. 13, Jul. 1, 2015.
Lu Yan, et al., "Q-plate enabled spectrally diverse orbital-angular-momentum conversion for stimulated emission depletion microscopy", Optica, vol. 2, No. 10, Oct. 2015.
Lu Yan, et al., "All-fiber STED microscopy illumination system", 2016 Optical Society of America, 2016.
Patrick Hoyer, et al., "Breaking the diffraction limit of light-sheet fluorescence microscopy by RESOLFT", PNAS, vol. 113, No. 13, pp. 3442-3446, Mar. 29, 2016.
Stefan W. Hell and Jan Wichmann, "Breaking the diffraction resolution limit by stimulated emission: stimulated-emission-depletion fluorescence microscopy", 1994 Optical Society of America, Mar. 7, 1994.
Min Gu, et al., "Breaking the diffraction-limited resolution barrier in fiber-optical two-photon fluorescence endoscopy by an azimuthally-polarized beam", Scientific Reports, Jan. 10, 2014.
Nenad Bozinovic, et al., "Control of orbital angular momentum of light, with optical fibers", 2012 Optical Society of America, compiled Apr. 30, 2012.
L. Paterson, et al., "Controlled Rotation of Optically Trapped Microscopic Particles", Science Magazine, vol. 292, May 4, 2001.
Abdulkadir Yurt, et al, "Effect of vector asymmetry of radially polarized beams in solid immersion microscopy", Optics Express, vol. 22, No. 6, published Mar. 21 and 24, 2014.
Nenad Bozinovic, et al., "Terabit-Scale Orbital Angular Momentum Mode Divison Multiplexing in Fibers", Science Magazine, vol. 340, Jun. 28, 2013.
Lars Rishoj, et al., "Experimental demonstration of intermodal nonlinear effects between full vectorial modes in a few moded fiber", Optics Express, vol. 21, No. 23, published Nov. 15 and 18, 2013.
Tomas Cizmar and Kishan Dholakia, "Exploiting multimode waveguides for pure fibre-based imaging", Nature Communications, Aug. 28, 2012.
Pu Wang, et al., "Far-field imaging of non-fluorescent species with subdiffraction resolution", Nature Photonics, vol. 7, Jun. 2013.
Y.Z. Ma, et al., "Fiber-modes and fiber-anisotropy characterization using low-coherence interferometry", Applied Physics B, May 7, 2009.
Siddharth Ramachandran, et al., "Generation and propagation of radially polarized beams in optical fibers", Optics Letters, vol. 34, No. 16, Aug. 15, 2009.
Jeffrey Demas, et al., "Generation of 10-kW Pulses at 880 nm in Commercial Fiber via Parametric Amplification in a Higher Order Mode", 2016 Optical Society of America, 2016.
G. Prabhakar, et al., "In-Fiber Monomode Octave-Spanning OAM Supercontinuum", 2016 Optical Society of America, 2016.
J. Demas, et al., "Intermodal nonlinear mixing with Bessel beams in optical fiber", Optica, vol. 2, No. 1, Jan. 2015.
Lu Yan, "Stimulated Emission Depletion Microscopy With Optical Fibers," dissertation of Lu Yan for Boston University College of Engineering, 2017.
Siddharth Ramachandran, et al., "Nonlinear generation of broadband polarisation vortices", Optics Express, vol. 18, No. 22, Oct. 25, 2010.
S. Pidishety, et al., "OAM Beam Generation using All-fiber Fused Couplers", 2016 Optical Society of America, 2016.
S. Ramachandran, et al., "On the scalability of ring fiber designs for OAM multiplexing", Optics Express, vol. 23, No. 3, Feb. 9, 2015.
L. Yan, et al., "Optical Fiber Vortices for STED Nanoscopy", 2013 Optical Society of America, 2013.
P. Gregg, et al., "Q-plates as higher order polarization controllers for orbital angular momentum modes of fiber", Optics Letters, vol. 40, No. 8, Apr. 15, 2015.
J. Demas, et al., "Sensing with optical vortices in photonic-crystal fibers", Optics Letters, vol. 37, No. 18, Sep. 15, 2012.
L. Yan, et al., "Single-aperture STED illumination using a q-plate and fiber", Optical Society of America, 2015.
B. Tai, et al., "Wideband nonlinear frequency conversion with OAM fiber", Optical Society of America, 2016.

* cited by examiner

OPTICAL IMAGING SYSTEM EMPLOYING VORTEX FIBER FOR MULTIPLE-MODE ILLUMINATION

STATEMENT OF GOVERNMENT RIGHTS

The invention was made with Government support under the following contracts awarded by the respective Federal agencies:
Grant no. N00014-13-1-0627 awarded by the Naval Research Laboratory
Grant no. ECCS-1310493 awarded by the National Science Foundation
Grant no. 1R21EY026410-01 awarded by the National Institutes of Health
The government has certain rights in the invention.

BACKGROUND

The present invention relates to the field of microscopy and other optical imaging systems, and in particular to "all fiber" optical imaging systems in which a multi-mode optical fiber is used to deliver distinct illumination optical signals. An example application includes stimulated emission depletion (STED) microscopy, wherein the illumination optical signals include separate excitation and depletion beams.

SUMMARY

Generally, the present disclosure relates to a vortex optical fiber for use in an illumination subsystem of an optical imaging system, such as a stimulated emission depletion (STED) microscopy system. The vortex optical fiber includes an elongated optically transmissive medium having a set of regions including a core region, a trench region surrounding the core region, a ring region surrounding the trench region, and a cladding region. The set of regions have a doping profile providing a $\Delta n_{eff}$ for vector modes in an $LP_{11}$ mode group of greater than $1 \times 10^{-4}$ in the visible spectral range so as to simultaneously guide stable Gaussian and orbital angular momentum (OAM) carrying modes at corresponding visible wavelengths.

In another aspect, the present disclosure relates to an optical fiber wherein the optical beams necessary for an application such as STED microscopy can be realized. In one embodiment the optical fiber comprises a core, a trench, a ring and a cladding. The core and the ring having higher refractive indices than the cladding and the trench separating the core and the ring with a lower refractive index than the core and the ring, preferably also lower than the cladding. The core can guide a fundamental mode $LP_{01}$ of a first light to become the Gaussian shaped excitation beam necessary for STED microscopy. The index profile of the optical fiber can be designed such that the fiber may have a refractive index step, corresponding to the ring, proximate to the peak amplitude value of the mode intensity profile of an $LP_{11}$ mode guided by the fiber.

The higher-order $LP_{11}$ mode comprises a linear combination of eigenmodes, including the cylindrically polarized $TM_{01}$ and $TE_{01}$ eigenmodes, and the mixed $HE_{21\ (even)}$ and $HE_{21\ (odd)}$ eigenmodes. The refractive index step of the ring is preferably sufficiently steep such that at least one of the cylindrically polarized $TM_{01}$ and $TE_{01}$ eigenmodes has an effective refractive index $n_{eff}$ that is sufficiently separated from the respective effective refractive index of the other eigenmodes to allow coupling to the at least one cylindrically polarized eigenmode with minimal coupling to the other eigenmodes. Similarly the refractive index step of the ring is preferably sufficiently steep such that the $HE_{21\ (even)}$ and $HE_{21\ (odd)}$ eigenmodes have an effective refractive index $n_{eff}$ that is sufficiently separated from the respective effective refractive index of the cylindrically polarized $TM_{01}$ and $TE_{01}$ eigenmodes to allow coupling to the mixed mode with minimal coupling to the other eigenmodes. In one embodiment the presently disclosed optical fiber is designed to have effective refractive index separation $\Delta n_{eff}$ of at least $1 \times 10^{-4}$ the $LP_{11}$ modes in the visible wavelength range, i.e. 400-700 nm. Further, the mode-field overlap with an ideal Gaussian beam is preferably greater than 80%, more preferably greater than 90%, even more preferably greater than 95%. Even further the present fiber is designed to have a cutoff wavelength for the $LP_{11}$ modes of less than 1000 nm, more preferably less than 950 nm, more preferably less than or equal to 930 nm. Also the fiber is preferably designed such that the cutoff wavelength for the $LP_{11}$ modes is separated from the wavelength of the depletion beam (i.e. the second light) by more than 200 nm. Further the cutoff wavelength for the next higher order modes, such as $EH_{11}$ and $HE_{31}$ is preferably separated from the wavelength of the depletion beam (i.e. the second light) by less than 50 nm.

When the $LP_{11}$ modes are separated they can carry orbital angular momentum to become the so called orbital angular momentum (OAM) modes. Under adequate polarization control an OAM mode can have the shape of a donut under high numerical aperture focusing, thereby being suitable for use as the depletion beam in STED microscopy. With careful phase engineering of the index profile, an optical fiber with a step index core and a step index ring can carry both the excitation beam and the depletion beam necessary for STED microscopy. Further careful phase engineering of the index profile can ensure that this can be provided across the visible spectral range (approx. 400-700 nm) where most available STED dyes are excited. Hence, the specific dye and the specific STED application determines the wavelengths of the excitation beam and the STED depletion beam and thereby the optical constraints on the optical waveguide used. As most dyes are in the visible spectral range an optical fiber for STED microscopy must be able to efficiently guide light in the visible spectral range.

Experiments have shown that the donut shaped depletion beam realized with the presently disclosed vortex fiber can provide an extinction ratio between the intensity at the center of the donut and at the peak are measured to less than −20 dB at 776 nm, which compare favorably to the desirable value of −13 dB for practical STED applications The presently disclosed fiber therefore provides stability of optical modes at visible wavelengths providing for a stable STED microscopy system operating in the visible domain. The presently disclosed fiber is also termed a vortex fiber because it is suitable for carrying vortex-fiber modes in the ring region.

In another embodiment the presently disclosed optical fiber is provided with a double clad design surrounding the central core and ring regions can create a multimode waveguide for collecting and propagating a signal, e.g. from an illuminated sample. A double cladding design can for example be provided by a low index primary coating surrounding a glass cladding. Low index polymer coatings are known from double clad fibers for guiding high power laser sources. A double cladding design, e.g. in the form of low index primary coating surrounding the cladding region, can be utilized for creating a high NA multimode waveguide in the cladding region. In this case it can be utilized for collecting the STED fluorescence signal that is generated in a sample being illuminated by the STED beams guided in the core and rings regions. The STED fluorescence signal can consequently be guided back through the multimode cladding. A low index cladding can also be provided by means of an air-cladding comprising air-holes as also exemplified in figures herein.

The present disclosure further relates to a method for illuminating a sample comprising the steps of: providing the presently disclosed optical fiber; providing a first beam in the fundamental $LP_{01}$ mode through the core region of the optical fiber; providing a second beam as one or more orbital angular momentum (OAM) modes guided through the ring region of the optical fiber; focusing the beams onto a sample to provide a Gaussian shaped excitation beam surrounded by a donut shaped depletion beam. This may be used for illumination in a STED procedure, i.e. the beams are focused on to the sample in order to generate a STED fluorescence signal from the sample.

Additionally, the present disclosure also relates to a method for performing STED microscopy comprising the steps of: providing the presently disclosed optical fiber; providing an excitation beam in the fundamental $LP_{01}$ mode through the core region of the optical fiber; providing a depletion beam as one or more orbital angular momentum (OAM) modes guided through the ring region of the optical fiber; focusing the beams onto a sample to provide a Gaussian shaped excitation beam surrounded by a donut shaped depletion beam in order to generate a STED fluorescence signal from the sample; and collecting the STED fluorescence signal. The STED fluorescence signal can be collected by normal bulk optic. However, as described above a low index coating may provide for the cladding region becoming a multimode waveguide with high numerical aperture such that the STED fluorescence can be collected and guided back through the same optical fiber.

In another aspect the present disclosure relates to STED microscopy system, comprising: an optical fiber as described above; a first light source for launching excitation light in the fundamental $LP_{01}$ mode in the core region of the optical fiber; a second light source for launching depletion light in the fundamental $LP_{01}$ mode in the core region of the optical fiber; a mode converter configured for converting the fundamental $LP_{01}$ mode of the depletion light into the higher order $LP_{11}$ mode thereby generating the depletion beam formed as one or more orbital angular momentum (OAM) modes propagating through the ring region of the optical fiber; focusing optics configured for focusing the excitation light and the depletion beam onto a sample to provide a Gaussian shaped excitation beam surrounded by a donut shaped depletion beam in order to generate a STED fluorescence signal from the sample; and a detector for detecting the STED fluorescence signal from the sample.

With the use of the presently disclosed optical fiber a STED microscopy system based thereon can be made compact and rugged. As the same optical fiber can be used for guiding the STED beams and for collecting the STED signal it opens for small footprint integration STED microscopy systems well-suited for tight environments, such as inside a human or animal body, for example in an endoscopic system.

Yet another aspect of the present disclosure therefore relates to an endoscopic system for STED microscopy, comprising the STED microscopy system as just described and an endoscope having a distal end for entering a bodily cavity, wherein at least a part of the optical fiber and the focusing optics is incorporated in the endoscope such that the excitation beam and the depletion beam are emitted from the distal end of the endoscope and the STED fluorescence signal is collected from said distal end of the endoscope.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views.

DETAILED DESCRIPTION

The entirety of U.S. provisional application 62/345,022 filed Jun. 3, 2016 and entitled "Optical Fiber For A STED Microscopy System" is incorporated herein by this reference thereto.

Figure 1:
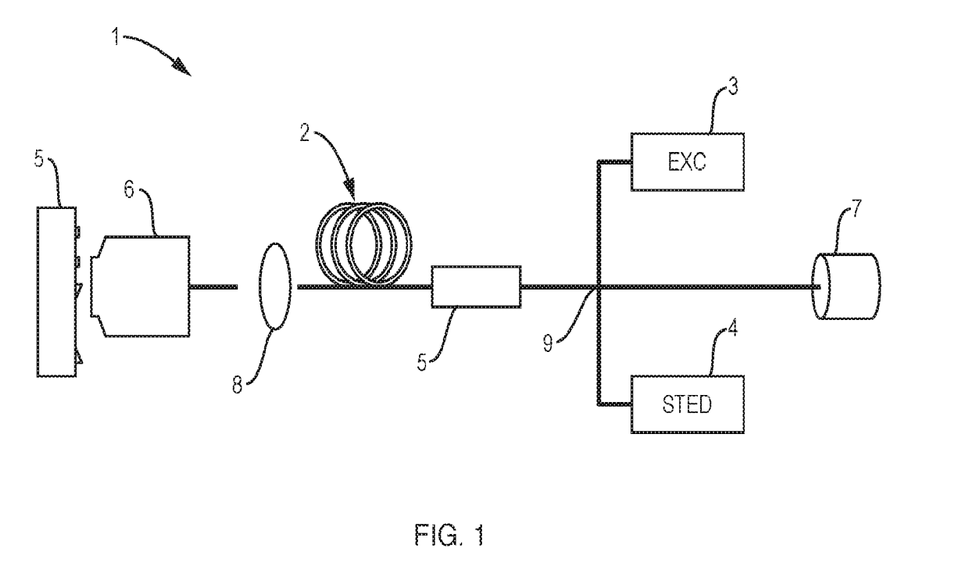
FIG. 1 is a block diagram of a stimulated emission depletion (STED) microscopy system.

FIG. 1 shows a schematic diagram of an embodiment of the presently disclosed STED microscopy system 1 comprising an optical vortex fiber 2 as disclosed herein comprising a multimode (MM) cladding defined by a low index coating. The system comprises a first light source 3 for launching excitation light in the fundamental $LP_{01}$ mode in the core region of the optical fiber 2; a second light source 4 for launching depletion light in the fundamental $LP_{01}$ mode in the core region of the optical fiber 2; a mode converter 5 configured for converting the fundamental $LP_{01}$ mode of the depletion light into the higher order $LP_{11}$ modes thereby generating the depletion beam formed as one or more orbital angular momentum (OAM) modes propagating through the ring region of the optical fiber 2; and focusing optics 6 configured for focusing the excitation light and the depletion beam onto a sample 5 to provide a Gaussian shaped excitation beam surrounded by a donut shaped depletion beam in order to generate a STED fluorescence signal from the sample 5. The microscopy system may also include a collimator (not shown) in front of the focusing optics. In the illustrated STED microscopy system 1 the STED fluorescence signal from the sample is collected by the numeral aperture formed by the cladding region of the optical fiber 2 such that the STED fluorescence signal is guided back through the MM cladding region. A tapered fiber coupler 9 for coupling the excitation light and the depletion light into the core region of the optical fiber and for separating the STED fluorescence signal propagating backwards in the cladding region of the optical fiber 2 is further provided. A detector 7 is provided for detecting the STED fluorescence signal from the sample 5.

Figure 2:
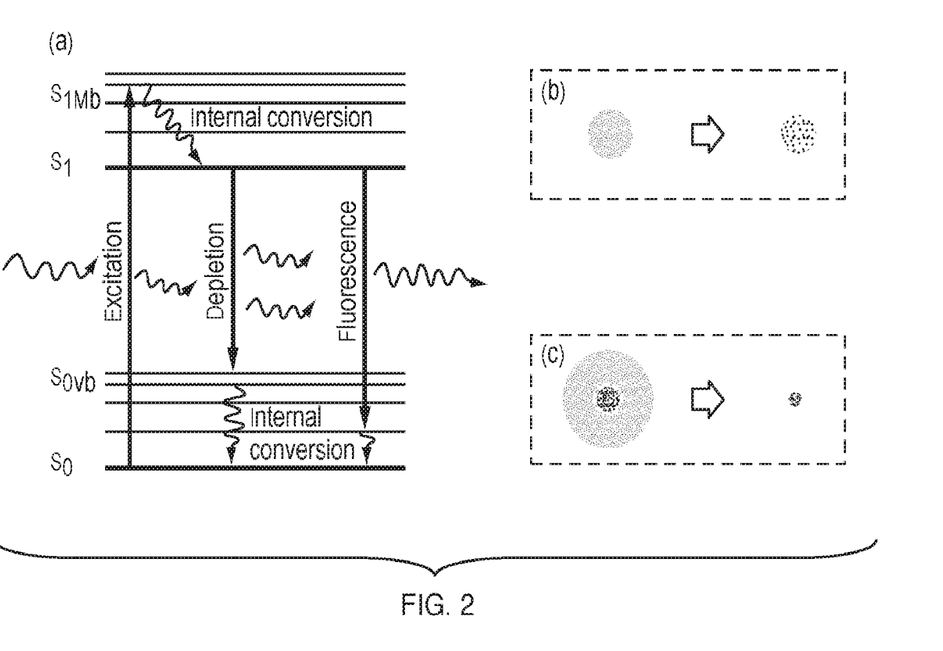
FIG. 2 is a schematic illustration of the STED principle.

FIG. 2 illustrates the principle of STED microscopy. Part (a) is an energy diagram for a fluorescent dye molecule as would be incorporated into a sample to be imaged by the STED microscope. Part (b) is a point spread function for conventional fluorescence microscopy, and part (c) is a point spread function for STED microscopy, illustrating the enhancement of resolution beyond the diffraction limit.

Referring to the energy diagram part (a) of FIG. 2, a fluorescence dye molecule at a ground state $S_0$ is excited by an excitation beam (also referred to herein as "excitation optical signal") to a first excited state $S_0$, and then rapidly decays to the ground level of the first excited state S1. When the molecule later decays (e.g., within 2-4 ns, a typical lifetime for fluorescence dyes) to the ground state $S_0$, it emits fluorescence photons that can be registered to form the image contrast. In the presence of a red-shifted laser beam called the depletion beam (or "depletion optical signal") whose energy matches the gap between $S_1$ and $S_0$, state $S_1$ is depopulated through stimulated emissions, emitting photons of the same wavelength as the depletion beam. With suitable intensity for the depletion beam, relative to the cross-section of the fluorescence molecules, the decay rate of the stimulated emission can exceed that of spontaneous emission, and therefore most molecules at state $S_1$ do not generate fluorescence but rather stimulated emission photons. Also, the depletion beam does not re-excite the molecule to the upper excited state due to an inherent energy mismatch.

Thus as illustrated in FIG. 2 the illumination light in the microscopy system has a spatially complex pattern of two separate beams or optical signals: (1) a Gaussian-shaped excitation beam, and (2) a ring-shaped (or donut-shaped) depletion beam, also referred to as a "STED beam", surrounding the excitation beam. Using this configuration, fluorescence dye molecules residing in the donut region are quenched through the stimulated emission, and only the fluorescence in the central area of the excitation beam is registered. This pattern of beams can be scanned over a sample to obtain a high-resolution image thereof.

Figure 3:
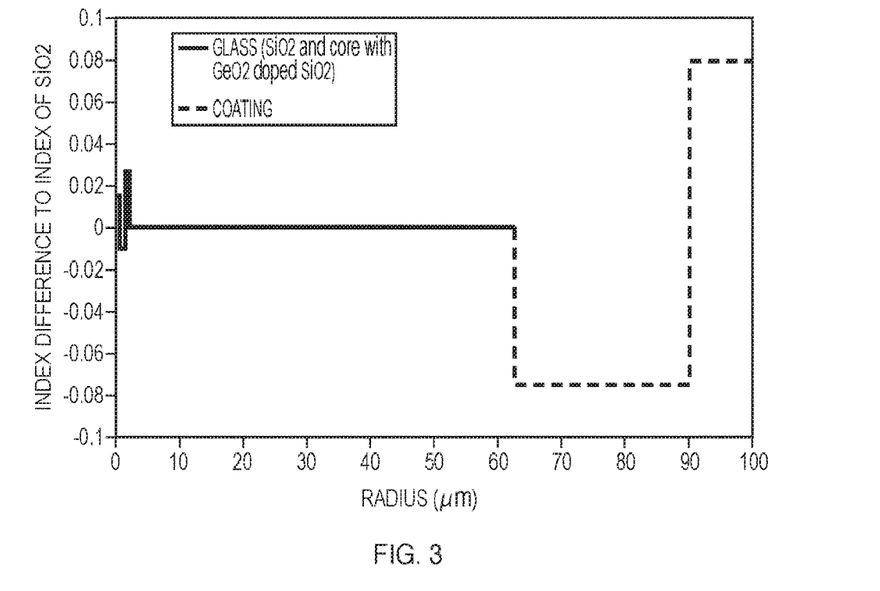
FIG. 3 is a plot of a refractive index profile of an optical fiber.

FIG. 3 shows a refractive index profile across the entire radius (1-100 um) of the fiber 2, which preferably includes a standard secondary (polymer) coating region surrounding the primary coating region, the secondary coating region having an inner radius equal to $r_{primary\ coating}$ and an outer radius that is equal to $r_{secondary\ coating}$, and a refractive index $n_{secondary\ coating}$ greater than $n_{cladding}$, wherein $\Delta n_{secondary\ cladding} = n_{secondary\ cladding} - n_{cladding}$. In one embodiment, the primary coating layer has $\Delta n_{primary\ coating} = -0.075$ beginning at the fiber radius of 62.5 micron and having a width of 27.5 micron; the numerical aperture of the cladding region is 0.46; and the secondary coating surrounding the primary coating is a standard fiber coating.

Figure 4:
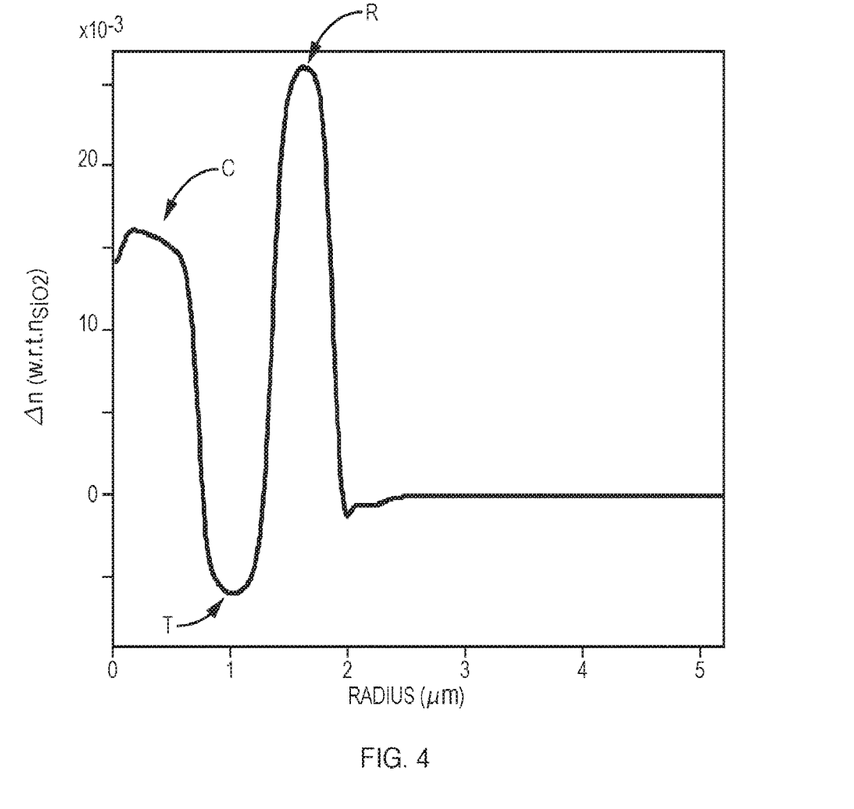
FIG. 4 is a plot of refractive index difference profile of an optical fiber near the core.

FIG. 4 shows a refractive index profile for a core region of the fiber 2 (0 to 5 um). In one embodiment, the optical fiber includes: a core region C having a core radius $r_{core}$ and a refractive index $n_{core}$, and an outer cladding region having an outer cladding radius $r_{core}$ and a refractive index $n_{cladding}$;

wherein $\Delta n_{core} = n_{core} - n_{cladding}$, and wherein $\Delta n_{core}$ in a first part of the core region is greater than 0. A trench region T may be provided surrounding the core region, the trench region having an inner radius equal to $r_{core}$ and an outer radius $r_{trench}$, and a refractive index $n_{trench}$ less than $n_{core}$, wherein $\Delta n_{trench} = n_{trench} - n_{cladding}$. A ring region R may be provided, preferably surrounding the trench region, the ring region having an inner radius equal to $r_{trench}$ and an outer radius $r_{ring}$, and a refractive index $n_{ring}$ greater than $n_{cladding}$, wherein $\Delta n_{ring} = n_{ring} - n_{cladding}$. Hence, the cladding refractive index $n_{cladding}$ is used as a reference value in determining the effective refractive index $\Delta n$ for the other fiber regions.

The values of some or all of $r_{core}$, $r_{ring}$, $r_{trench}$, $r_{cladding}$, $\Delta n_{core}$, $\Delta n_{trench}$ and $\Delta n_{ring}$ are preferably selected such that the optical fiber has a refractive index profile comprising a steep refractive index proximate to a peak amplitude value of a mode intensity profile of a fundamental $LP_{01}$ mode of a first light propagating through the optical fiber and a steep refractive index proximate to a peak amplitude value of a mode intensity profile of higher-order $LP_{11}$ modes of a second light propagating through the optical fiber. The higher-order $LP_{11}$ modes comprise a linear combination of modes, including cylindrically polarized $TM_{01}$ and $TE_{01}$ modes and mixed $HE_{21\ (even)}$ and $HE_{21(odd)}$ modes, such that at least one of the cylindrically polarized modes preferably has an effective refractive index sufficiently separated from effective refractive indices of the mixed modes to allow for coupling of the second light to the at least one cylindrically polarized mode with minimal coupling to the mixed modes or for coupling of the second light to the mixed modes with minimal coupling to the cylindrically polarized modes.

In one embodiment the refractive index difference profile near the core region can include $\Delta n_{core} = 0.016$, $r_{core} = 0.8$ micron, $\Delta n_{trench} = -0.007$, $r_{trench} = 1.3$ micron, $\Delta n_{ring} = 0.026$, $r_{ring} = 1.9$ micron.

When designing the fiber profile, the effective index separation $\Delta n_{eff}$ of the $LP_{11}$ modes is of prime importance and is mainly determined by refractive indices and widths of core, trench and ring, providing a very large parameter space for the fiber design. It can be noted that an increased index of the ring provides a large $\Delta n_{eff}$ and resulting tighter confinement of OAM modes. However, increasing the ring index makes the fundamental mode in the core more ring-like (i.e. more non-Gaussian) because of the tighter confinement. There is a trade-off between having large $\Delta n_{eff}$ and having a Gaussian-like fundamental mode. Increasing the index of the core will result in more Gaussian-like fundamental mode but it also decreases the effective index difference $\Delta n_{eff}$. More Gaussian-like fundamental mode can also be adjusted by varying the radius of the core. When optimizing the design for high $\Delta n_{eff}$ and Gaussian-like fundamental mode, the index of the trench can be fixed. In the end the trench parameters can be tuned to control the cutoff wavelength of the higher order modes since it has a much smaller effect on $\Delta n_{eff}$ compared to other parameters. A vector mode solver can be used to numerically simulate different fiber designs.

Hence, $\Delta n_{core}$ of the fiber index profile may be at least $5 \times 10^{-3}$, or at least $10 \times 10^{-3}$, preferably at least $15 \times 10^{-3}$. The radius of the core region $r_{core}$ is preferably less than 1 micron, mostly in order to provide for single mode operation in the visible wavelength range.

The trench provides a difference in refractive index between the core region and the ring in order to separate the light propagating in core and ring, respectively. The refractive index of the trench may be close to the index of the cladding. However, $\Delta n_{trench}$ less than 0, or less than $-2\times 10^{-3}$, preferably less than $-5\times 10^{-3}$ in order to further increase the height of the step index profiles of the core region and the ring region. The width of the trench region is mostly determined by the propagation constrictions on the core region and the ring. The width of the trench may be less than 1 micron. The selection of the refractive index and the width of the trench can be used to fine tune the cutoff wavelength of the $LP_{11}$ modes.

A second outer trench may be provided surrounding the ring region. The second trench can also be down-doped. The second trench may have a width and $\Delta n$ substantially corresponding to the inner trench.

Figure 5:
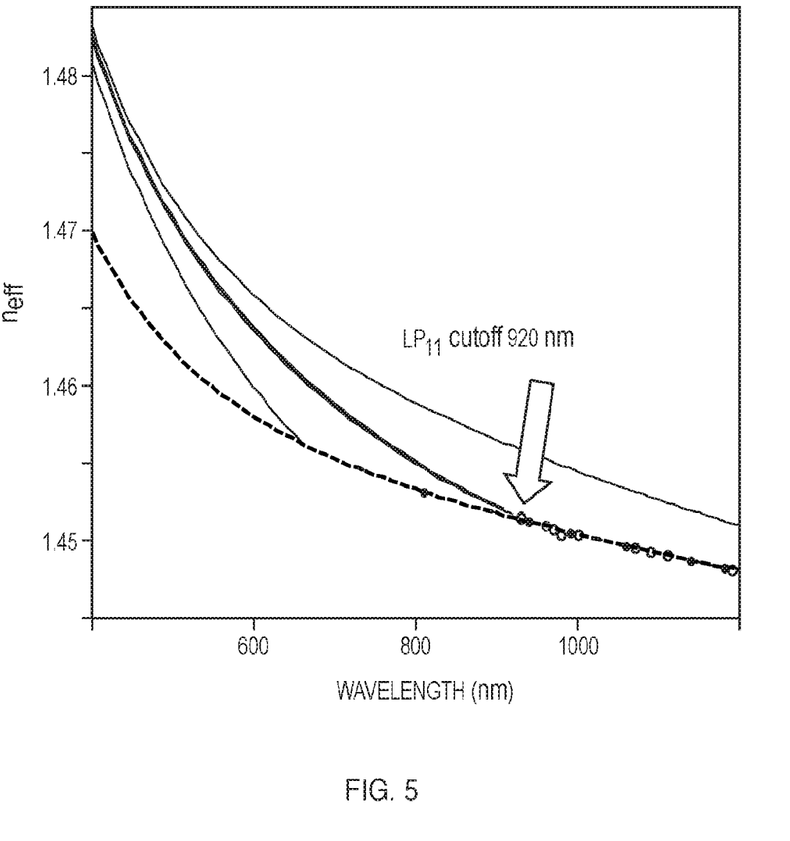
FIG. 5 is a plot of effective refractive index as a function of wavelength for certain modes.

FIG. 5 shows $n_{eff}$ as a function of wavelength for different modes, illustrating a cutoff wavelength of 930 nm for the $1^{st}$ higher order mode (HOM) group.

Figure 6:
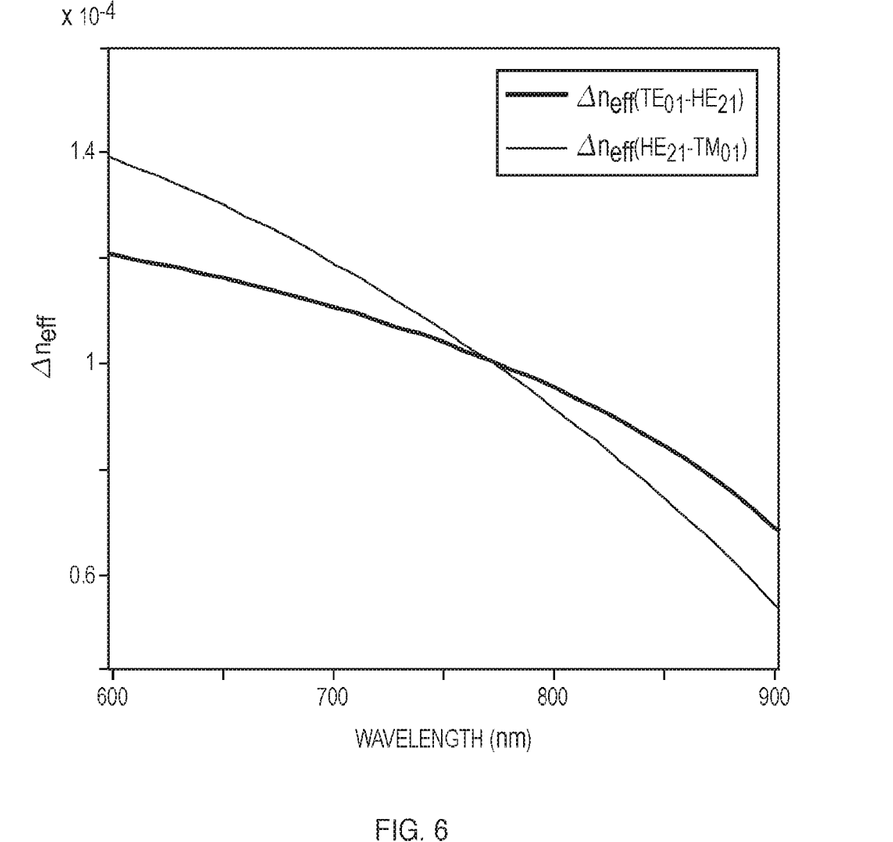
FIG. 6 is a plot of effective index separation $\Delta n_{eff}$ for an optical fiber.

FIG. 6 shows effective refractive index difference $\Delta n_{eff}$ for the cylindrically polarized $TM_{01}$ and $TE_{01}$ eigenmodes and the mixed $EH_{21\ (even)}$ and $HE_{21\ (odd)}$ eigenmodes. The ring design can provide for a polarization-maintaining fiber (PMF) that vastly increases the difference between the propagation constants of the cylindrically polarized $TM_{01}$ and $TE_{01}$ eigenmodes and those of the mixed $EH_{21\ (even)}$ and $HE_{21\ (odd)}$ eigenmodes. The optical fiber is polarization-maintaining even though it is strictly cylindrically symmetric. With a significantly distinct propagation constant, it is possible to couple to any of the eigenmodes with high modal purity. The width of the ring region and $n_{ring}$ is therefore preferably selected to provide an effective refractive index separation between the at least one cylindrically polarized mode and the mixed modes (and vice versa) of at least a $10^{-4}$, preferably also across the visible spectral range. This degree of separation is illustrated in FIG. 6.

The optical fiber is designed such that the ring region is located proximate to the amplitude peaks of the mode intensity profile of the scalar $LP_{11}$ mode. The ring effective refractive index $\Delta n_{ring}$ should have a value that is sufficiently high to cause the desired separation of the propagation constants of the $LP_{11}$ eigenmodes. $\Delta n_{ring}$ may be selected to be greater than $\Delta n_{core}$. Preferably, $\Delta n_{ring}$ is at least $15\times 10^{-3}$, or at least $20\times 10^{-3}$, most preferably at least $25\times 10^{-3}$. The radius of the ring $r_{ring}$ may be less than 4 microns, or less than 3 micron, or less than 2 microns, i.e., the width of the ring region may be less than 1 micron.

Fiber Cladding and Coating

The presently disclosed optical fiber may be fabricated from $SiO_2$ or other suitable material, using a modified chemical vapor deposition (MCVD) technique, or other suitable technique. The ring region and the core region may be formed by doping with a suitable index-raising dopant, or mixture of dopants, such as $GeO_2$, or the like. A negative index of the trench region can be achieved by use of fluorine. The cladding may be selected to be normal un-doped $SiO_2$. The optical fiber as disclosed herein may be designed to have a standard outer diameter of 125 microns making it easy to handle and splice to standard optical fibers.

As previously described the optical fiber further comprises a primary coating region surrounding the cladding region, the primary coating region having an inner radius equal to $r_{cladding}$ and an outer radius that is equal to $r_{primary\ coating}$. The refractive index $n_{primary\ cladding}$ is preferably less than $n_{cladding}$, wherein $\Delta n_{primary\ cladding} = n_{primary\ cladding} - n_{cladding}$. The width of the cladding region may be at least 30 or at least 50 microns. The width of the primary coating region may be at least 10 micron, or at least 20 micron. And $\Delta n_{primary\ coating}$ may be selected to be less than $-30\times 10^{-3}$, or less than $-40\times 10^{-3}$, or less than $-50\times 10^{-3}$, preferably less than $-60\times 10^{-3}$.

The refractive indices $n_{cladding}$ and $n_{primary\ coating}$ and the widths of the cladding region and the primary coating region may therefore be selected such that the numerical aperture of the cladding region is greater than 0.40, or greater than 0.43, preferably greater than or equal to 0.46. A STED fluorescence signal can thereby be collected by the numeral aperture formed by the cladding region of the optical fiber such that the STED fluorescence signal can be guided back through the multimode cladding region of the optical fiber. Having a low index cladding as herein disclosed therefore facilitates that a STED microscopy system may be made more compact. By guiding the STED fluorescence signal back through the cladding a beam splitter and a detector placed close to the focusing optics can be avoided. Instead a detector can be placed far behind the focusing optics.

Mode Conversion

The depletion beam can be launched in the core of the optical fiber in the fundamental $LP_{01}$ mode. A mode converter is then necessary to convert the $LP_{01}$ to the higher order $LP_{11}$ modes. This can be provided by means of a mode converter. The mode conversion may be provided by an external micro-bend grating which can also be used with the presently disclosed fiber design. However, a more rugged and compact solution is an UV long period grating inscribed in the core to provide mode conversion of the second light between the fundamental $LP_{01}$ input mode and the higher-order $LP_{11}$ modes. When the high index of the core of the presently disclosed optical fiber, is provided by Ge doping, the UV sensitivity of the core is increased making the UV LPG even more attractive. With an UV LPG with a length of less than 40 mm the mode conversion may be achieved with an extremely high purity providing a conversion efficiency of more than 95%, even more than 99.7%, and the insertion loss may be less than 0.1 dB. In the examples described herein a 31 mm long tilted long period grating was UV inscribed into the fiber to achieve a conversion efficiency of more than 99.7%.

Other types of suitable mode converters that can be used are acousto-optically generated fiber gratings, q-plates, spatial light modulators (SLM) and metasurfaces.

Illumination, Imaging and Microscopy Systems

Super-resolution microscopy using stimulated emission depletion (STED) creates sub-diffraction limit features by altering the effective point spread function of the excitation beam using a second donut shaped light beam that suppresses fluorescence emission from fluorophores located away from the center of excitation. The suppression of fluorescence is achieved through stimulated emission that occurs when an excited-state fluorophore encounters a photon that matches the energy difference between the ground and excited state. Upon interaction of the photon and the excited fluorophore, the molecule is returned to the ground state through stimulated emission before spontaneous fluorescence emission can occur. Thus, the process effectively depletes selected regions near the focal point of excited fluorophores that are capable of emitting fluorescence.

In a conventional confocal microscope, the full-width-at-half-maximum (FWHM) of the focal point (d) of a propagating beam with $\lambda$ wavelength through a lens with numerical aperture of NA is approximated to be: $d\sim\lambda/(2NA)$. Using the highest numerical aperture available today, this translates to about ~200-300 nm in the lateral direction (x,y) and ~500-700 nm in the axial direction (z) with visible light. This is the diffraction limited resolution as defined by the point spread function (PSF).

The spatial resolution of a STED microscopy system with a doughnut-shaped Gauss-Laguerre depletion beam is given by equation the equation $d \sim \lambda/(2NA(1+I/I_s)^{1/2})$. In this equation, I is the maximum intensity of the STED beam and Is saturation intensity characteristic of the dye. It is clear that the diffraction limit is obtained for I=0. Overcoming the diffraction limit is obtained by letting I approach infinity. Basic STED as described above does not improve axial resolution. However, it a STED microscopy, the FWHM of the PSF may easily be around 50 nm, i.e. a factor of around 4-5 times less than a confocal microscope.

As illustrated above, the point spread function (PSF) is an important parameter that defines the performance of a STED microscopy system. One way to define the PSF is by means of the extinction ratio defined as the ratio between the intensities at the center of the donut and at the peak, respectively. The depletion beam typically requires an extinction ratio of about −13 dB for proper STED imaging. A great advantage of the fiber based STED illumination as disclosed herein is that it provides a central intensity extinction ratio down to −19 dB, even down to −20.5, thus far better than required.

In a STED microscopy systems and particular in endoscopic systems, based on fiber optics, it is of great importance that the fiber can be bend without modifying the performance of the STED microscopy, hence without modifying the PSF. By the presently disclosed STED illumination system, there is provided a PSF that is highly bend-resistant as described below with reference to FIG. 7.

Several technical features of STED microscopy system may be present in order to optimize the performance of the herein disclosed STED microscopy system. E.g. one or more polarization controllers may be provided for controlling the content of the OAM mode(s). The presently disclosed STED illumination/microscopy system may further comprise a collimator in front of the focusing optics. Focusing may be performed after a step of collimating the Gaussian shaped excitation beam and the doughnut shaped depletion beam. The step of focusing may furthermore be performed by using a gradient-index (GRIN) objective. This can help facilitate implementation in an endoscopic system.

A standard fiber coupler can be used for coupling the excitation light and the depletion light into the core region of the presently disclosed STED optical fiber. Similarly a fiber coupler, such as a tapered fiber coupler, can be used for separating the STED fluorescence signal propagating backwards in the cladding region of the optical fiber and coupling the STED fluorescence signal into a separate MM optical fiber.

Figure 7:
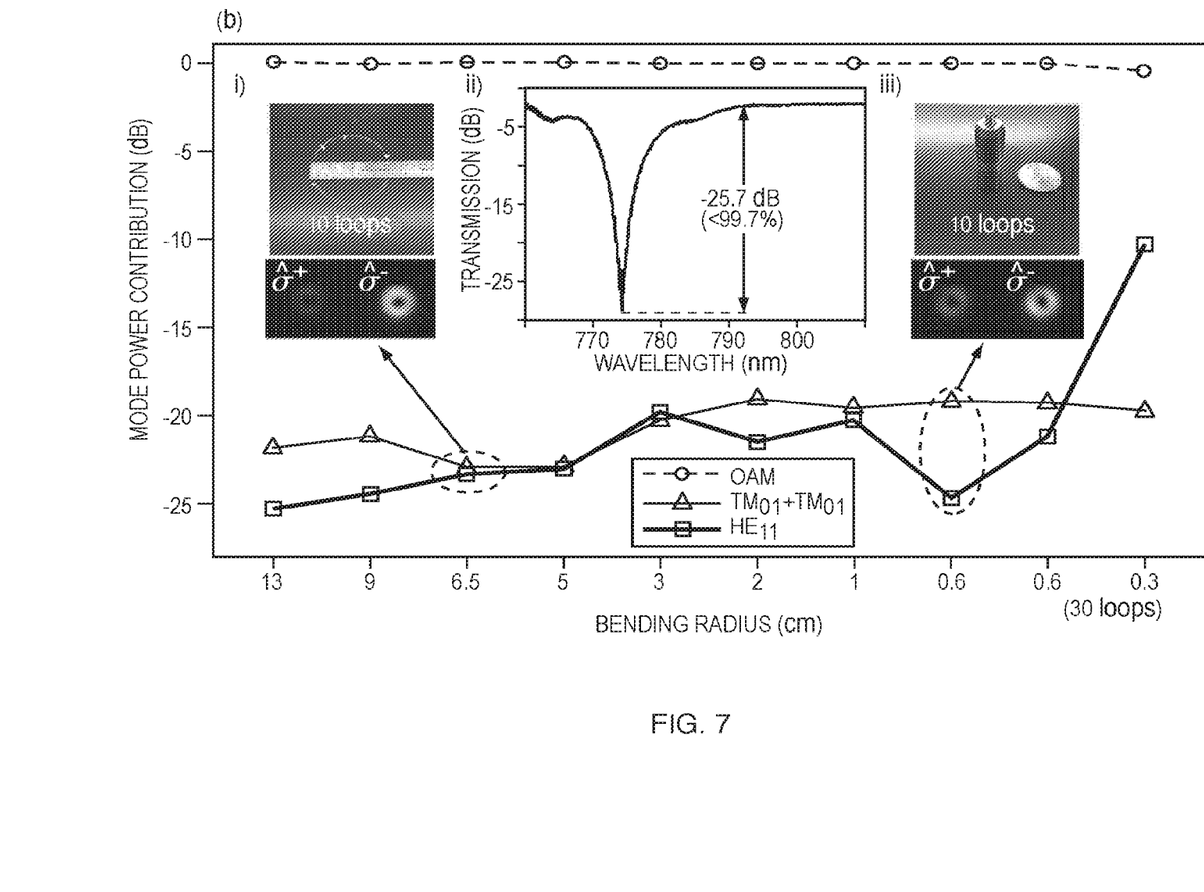
FIG. 7 is a plot of example extinction ratios of a depletion beam for different bend radii of an optical fiber.

FIG. 7 shows mode purity for different bending radii from 13 cm down to 0.3 cm of the vortex fiber. The OAM mode is at the top depicted with circles, the $TE_{01}$ and $TM_{01}$ modes depicted with triangles and the remain of the fundamental mode $HE_{11}$ with squares. Insets left i) and right iii) show pictures of coiled vortex fiber together with a ruler and a standard Ø½ inch optical post respectively (top), and the corresponding OAM mode images with circular polarization projections $\hat{\sigma}+$ and $\hat{\sigma}-$ (bottom). The middle inset (iii) of shows the transmission spectrum of the UV grating, revealing a mode conversion efficiency of 99.7%.

Spatial interferometry ("ring technique") is used to analyze mode purity by projecting the output of the fiber into two circular polarizations $\hat{\sigma}+$ and $\hat{\sigma}-$ using a quarter waveplate and a polarizing beam displacer and performing spatial Fourier analysis on the azimuthal intensity profiles to obtain mode purities. As described above the insets (i) and (iii) in FIG. 7 show pictures of the coiled vortex fiber (top) and the corresponding near-field mode images (bottom), respectively. As seen from the curves the OAM mode stays over 19 dB (98.7%) pure with bending radius down to 6 mm. Bends sharper than 6 mm (radius) induce significant bend loss, but in any case are much tighter than the bend specifications for typical microscopes or endoscopes.

Figure 8:
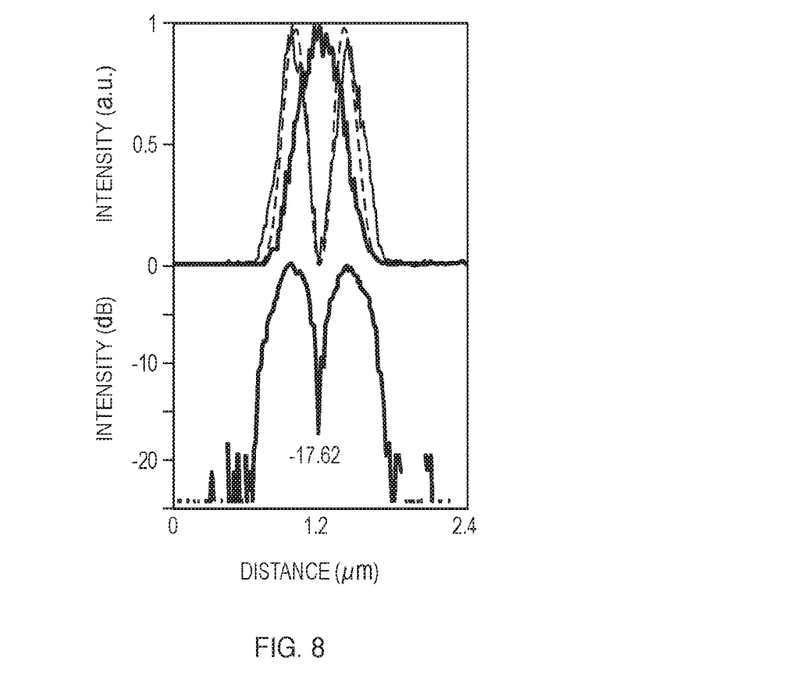
FIGS. 8 and 9 are plots of point spread function profiles.
Figure 9:
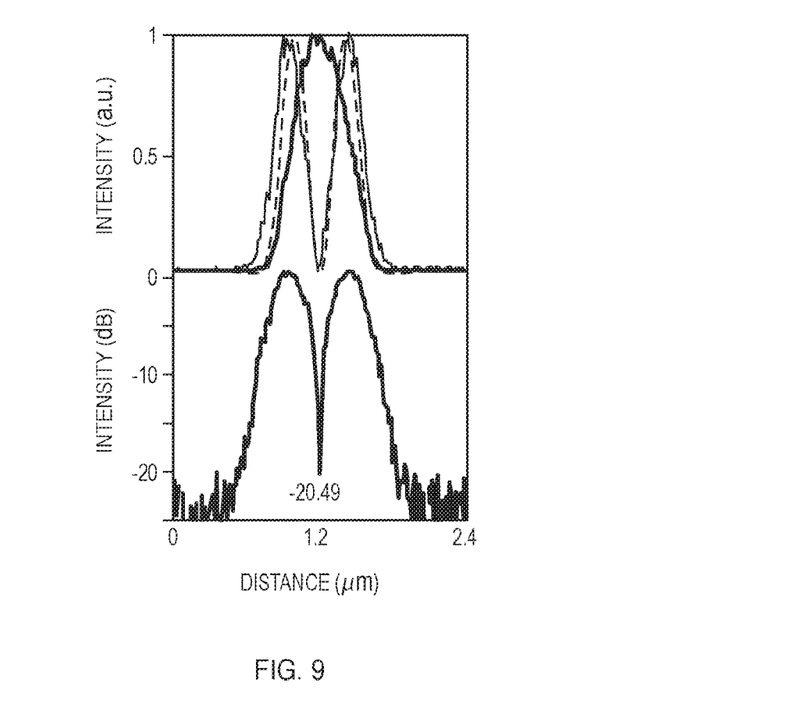

FIGS. 8 and 9 show point spread function profiles for the vortex fiber of example 1 with bending radius of (a) 6.5 cm (10 loops); and (b) 0.6 cm (10 loops). Line-cut profiles of the excitation and the STED beams in linear scale (top) are along dashed lines depicted in the lateral planes of PSF images. The results match with simulations (dashed blue lines). STED beam profiles are also plotted in dB scale (bottom) to elucidate extinction ratio. Scale bar: 500 nm.

For bend radii of 6.5 cm and 6 mm, the PSF is measured for the excitation and STED beams, respectively, by scanning a sample of gold beads (150 nm gold nanoparticle) and detecting the scattered light. The two PSFs are spatially well aligned in both directions. The full width of half maximum of the excitation PSF is ~382 nm, and that of the dark center of the donut is ~235 nm. These values compare well with theoretical estimates which are shown with dashed blue lines and are representative of similar measurements with state of the art free-space systems. The extinction ratios, defined as the ratios between intensity at the center and at the peak are measured to be −17.6 dB and −20.5 dB, respectively, which compare favorably to −13 dB, the oft-quoted desirable value for practical STED applications.

Figure 10:
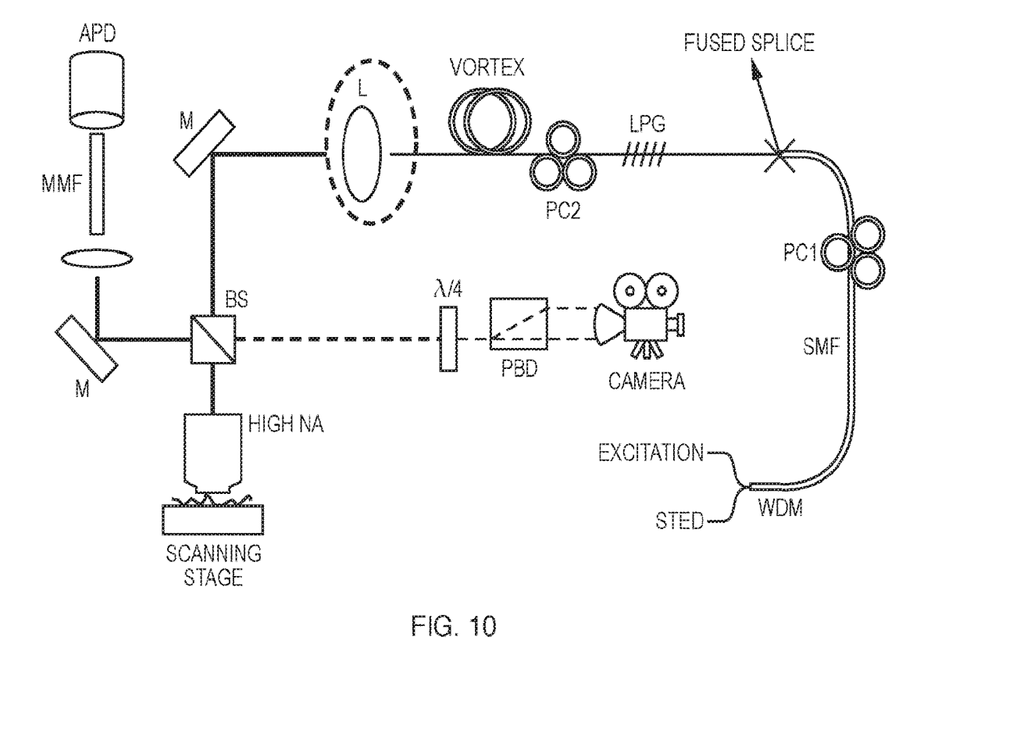
FIG. 10 is a block diagram of a STED microscopy system.

FIG. 10 shows a system schematic of an exemplary embodiment of a STED microscopy system according to the present disclosure. The excitation beam ($\lambda$=632.8 nm, HeNe laser) and the STED/depletion beam ($\lambda$=776.34 nm, Ti:Sapphire laser) are combined into a single mode fiber (SMF) with in-line fiber polarization controller (polcon) using a fiber coupler in the form of a wavelength division multiplexer (WDM). The SMF is spliced to an embodiment of the presently disclosed vortex fiber in which a 31 mm long tilted UV-LPG is inscribed to generate the OAM mode. The first polarization controller PC1 can be used to generate circularly polarized depletion light helping to ensure that the OAM modes generated by the LPG carry angular momentum such that the depletion beam incident on the sample is donut shaped. Combined losses (from the splice and grating) are as low as 0.8 dB, with additional improvements potentially possible via splice optimization. Following the grating, a second fiber polarization controller (PC2) is used to control the content of spin-orbit aligned OAM modes (L=+1 and L=−1), both of which generate a dark center under high NA focusing condition, and hence are suitable for STED. After approx. 5.1 m of coiled vortex fiber, the output pigtail is clamped using a bare fiber adapter. The beam output is collimated using an objective (10×), and focused by a high NA objective (60×/1.35) on to a sample plane. The vortex fiber used here is provided with standard coating layers and the STED signal can consequently not be guided back through the cladding. A beam splitter (BS) is therefore provided to couple the STED fluorescence signal into a standard multimode fiber (MMF) in into a photodetector (APD). The beams are imaged using a quarter wave plate ($\lambda$/4), a polarization beam displacer (PBD) and a camera.

Figure 11:
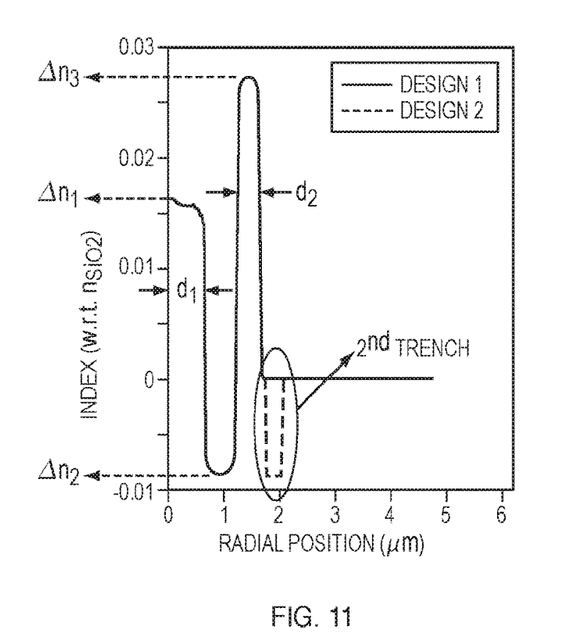
FIG. 11 is a plot of vortex fiber index profiles.

FIG. 11 illustrates a favorable design parameter space for an all fiber STED microscope using vortex fibers that work in the visible wavelength range where most STED fluorescence dyes are employed. The following criteria may be used to evaluate new vortex designs:

Enhanced $\Delta$neff, preferably greater than $1\times10-4$ between $LP_{11}$ modes group in the visible wavelength range, i.e. 400~700 nm.

Gaussian-like fundamental mode, i.e. the mode field overlap with an ideal Gaussian beam is greater than 90%.

Appropriate cutoff wavelengths for $LP_{11}$ modes group (>200 nm apart from the STED wavelength), and for the next higher order modes (e.g. $EH_{11}$ and $HE_{31}$; <50 nm apart from the STED wavelength).

Fiber grating pitch for efficient mode conversion should be accessible by UV or microbend induced or acousto-optically generated gratings.

Among these criteria, $\Delta$neff is of prime importance. According to the vector wave equation, the separation between $LP_{11}$ modes group is mainly determined by the parameters showed in FIG. 1, i.e. $\Delta$n1, $\Delta$n2, $\Delta$n3, d1, and d2, and the appearance of the 2nd down-doped trench. The fiber design has a huge parameter space. The functional relationship between these parameters and fiber properties are complicated, and the parameters are most often coupled to one or more fiber properties, for example:

To have a large $\Delta$neff, we first increase the index of the ring $\Delta$n3. The high (ring) index results in tighter confinement for OAM modes. As expected, increasing the ring index inevitably makes the fundamental mode more ring-like because of the tighter confinement. There is a trade-off between having large $\Delta$neff and getting the Gaussian-like $HE_{11}$ mode.

Increased $\Delta$n1 will result in better Gaussian-like fundamental mode but it also decreases the effective index difference $\Delta$neff.

Higher $\Delta$n3 lower $\Delta$n2 will increase $\Delta$neff however change the fundamental mode into ring-shape. We intentionally fix the index of the fluorine down-doped region ($\Delta$n2) when searching for parameters to achieve the first two goals described above, and leave it as a tuning parameter (sometimes together with fine tuning of the core index $\Delta$n1 as well) to control the cutoff wavelength of the higher order modes since it has a much smaller effect on $\Delta$neff compared to other parameters.

As $\Delta$n1~$\Delta$n3 are changed, the core radius d1 need to be adjusted to get better Gaussian-shaped fundamental mode.

As $\Delta$n3 is changed, we have to decrease d2 correspondingly to get larger $\Delta$neff.

Figure 12:
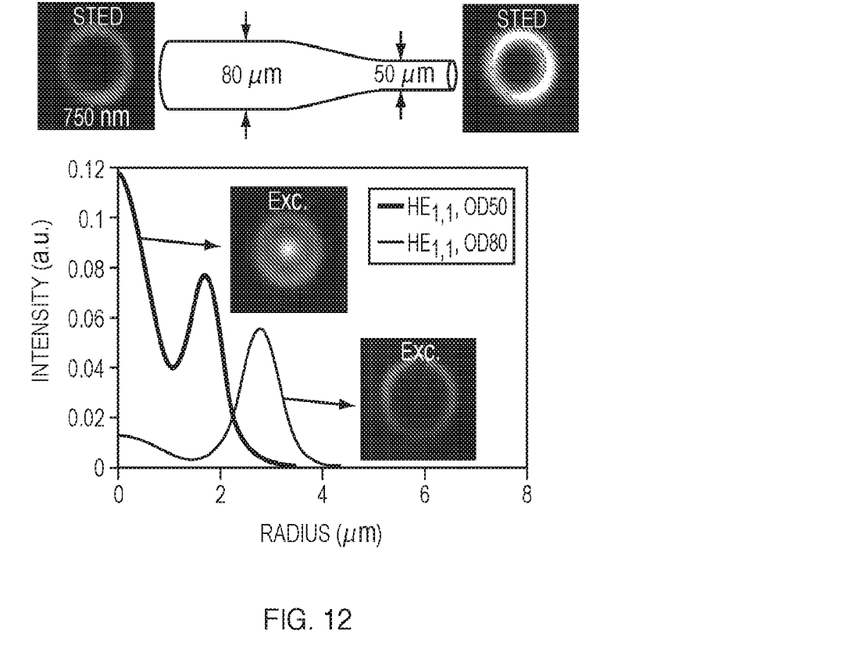
FIG. 12 is a schematic illustration of generating excitation and depletion beams using a taper.

FIG. 12 illustrates that the $HE_{1,1}$ mode at the excitation wavelength can be reshaped by changing the size of the fiber output, e.g., by tapering. This process involves mounting the fiber on motorized translation stages and heating and melting the fiber to a certain extent by a moving electric-arc assembly. By carefully controlling the velocity profiles of the two stages and arc assembly, and the power of the electric arcs, an adiabatic fiber taper consisting of two transition regions of 10 mm, and a waist of 10 mm can be made. The waist is cleaved in the middle to create an output with smaller OD, chosen such that the $HE_{1,1}$ mode at the excitation wavelength becomes Gaussian-like while the OAM mode at the depletion/STED wavelength is still well guided and $\Delta$neff does not decrease too much. FIG. 12 shows a schematic of an OD 50 um taper and simulated intensity profiles of two fundamental modes from fiber outputs with OD of 50 um (taper) and 80 um (non-taper). The two STED beam images on the top also indicate that the OAM mode at the STED wavelength of 750 nm is not distorted by the output taper, which can be confirmed by characterizing the PSF of this beam.

Figure 13:
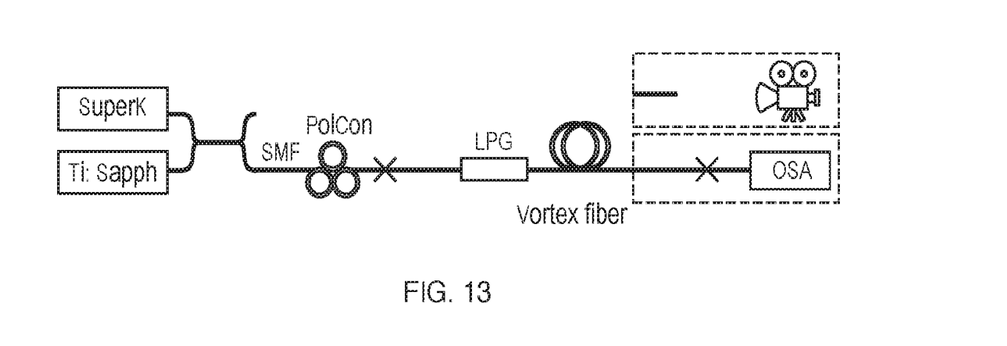
FIG. 13 is a schematic diagram of a microscopy system employing a long period grating (LPG) for mode conversion.

FIG. 13 illustrates use of a long period grating (LPG) as a mode conversion element, placed before the vortex fiber. This arrangement may be applied to the microscopy arrangements described elsewhere (e.g., FIGS. 1, 10, 14) to effect the desired mode conversion.

Figure 14:
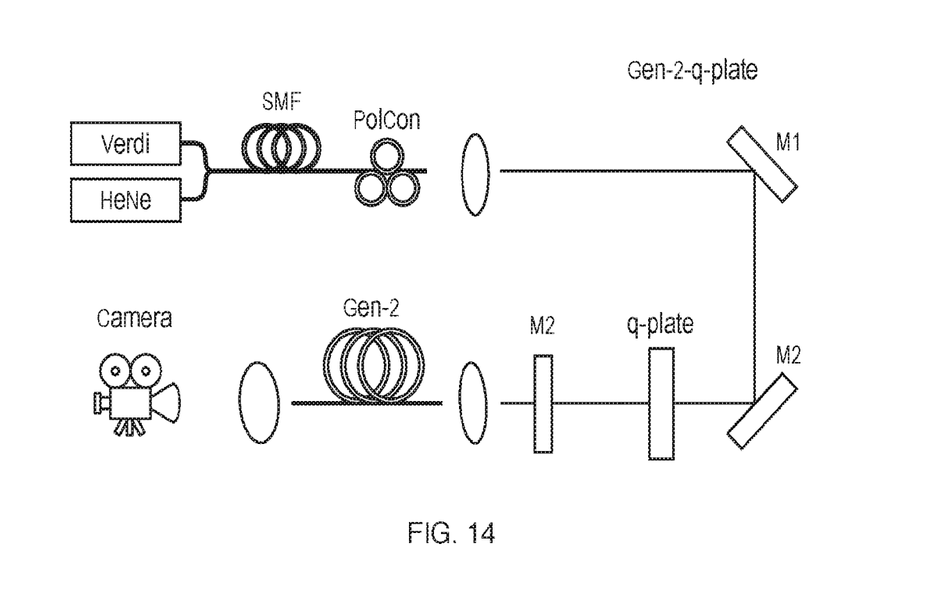
FIG. 14 is a schematic diagram of a microscopy system employing a q-plate for mode conversion.

FIG. 14 shows an arrangement employing a q=½-plate to simultaneously excite an OAM mode at $\lambda_{STED}$=632.8 nm, and an intrinsically co-aligned Gaussian-like fundamental mode at $\lambda_{exc}$=532 nm in a vortex fiber. A laser beam from a CW HeNe ($\lambda$=632.8 nm) and a Verdi ($\lambda$=532 nm) are combined into an SMF with an in-line fiber PolCon. The combined beam is collimated and passes through a q=½-plate and an achromatic half-wave plate. These devices in tandem convert a Gaussian beam into an OAM beam with a controllable efficiency determined by an AC voltage bias of the q-plate provided by a function generator (not shown). The resultant beams are then free-space coupled into the vortex fiber, in which the OAM mode and Gaussian-like fundamental mode stably co-propagate. The fiber output is near-field imaged using a CMOS camera.

In this example, an AC bias of 1.611 V (f=2 kHz) causes the q-plate to fully convert the depletion beam into a donut at 632.8 nm, while leaving the excitation beam at 532 nm unconverted. After about 3 m of propagation in the fiber, the OAM mode purity is better than −15 dB.

Figure 15:
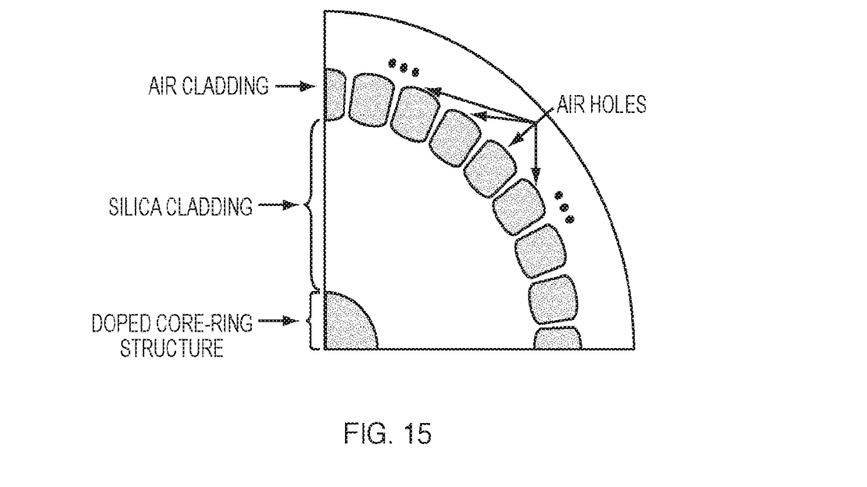
FIG. 15 is a schematic depiction of a fiber having an air cladding.

FIG. 15 is a schematic of a vortex fiber design with an air cladding. We suspect that the background light is largely coming from the cladding guiding region and possibly from the dopants and polymer jacket based on the preliminary results, therefore new designs that may address it could be introducing an inner cladding waveguide structure, formed by the silica cladding of current vortex fiber and an extra layer of so-called air-cladding consisting of air holes which has been used in several specialty fibers. This may well confine the excitation light and the backward-propagating fluorescence into an all-glass cladding, therefore significantly reduce the background light from the dopant as well as polymer jacket.

Figure 16:
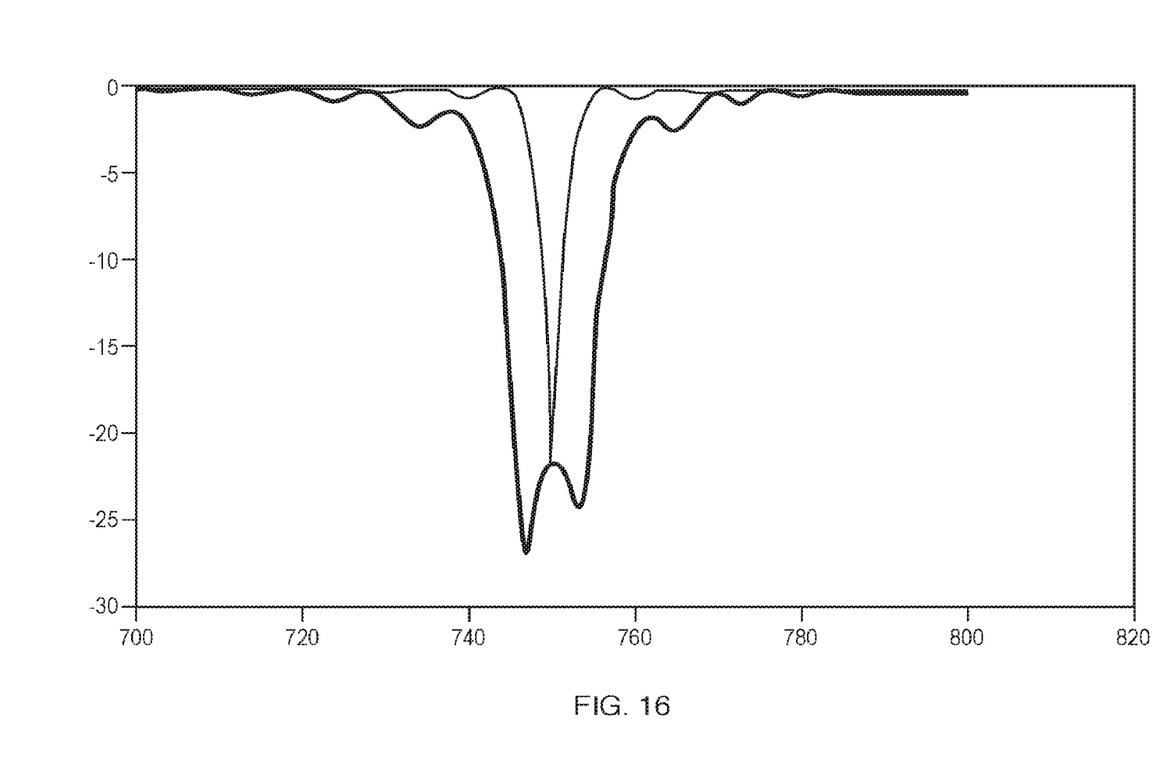
FIG. 16 is a plot of a response characteristic of a chirped grating used for mode conversion.

FIG. 16 illustrates the use of a chirped grating to achieve high conversion efficiency over large bandwidth.

PARTICULAR ALTERNATIVES

In addition to specific elements and features described above, the following are specific alternatives that may be employed:

1. Fiber designs incorporating a taper at the output end of the fiber such that mode reshaping to attain Gaussian excitation and donut shaped OAM beam even if the fiber itself doesn't have the desired mode shapes.

2. Two-photon excitation. Because $LP_{01}$ mode is at longer wavelength, for example 2× the excitation wavelength, and thus has less issue with the mode being ring-shaped, two photon excitation may be explored to achieve suitable Gaussian-shaped excitation pattern without the need to reshape the $LP_{01}$ mode at the one photon excitation wavelength.

3. The fibers could be used for excitation alone as well as for the excitation and signal collection/detection.

4. Ring core only fiber designs where mode separations for the vector modes remain as above, but the $LP_{01}$ mode is a ring shaped mode too. High NA focusing will convert the uniformly polarized $LP_{01}$ mode into a Bessel beam at sample/focal plane, which has the required high intensity center spot required of the excitation beam.

While the above disclosure provides a description primarily with reference to application in STED microscopy, those skilled in the art will appreciate that the disclosed techniques may be employed in a variety of imaging systems including STED, light sheet microscopy, multi-photon microscopy, pump-probe microscopy, or other light manipulation techniques.

While various embodiments of the invention have been particularly shown and described, it will be understood by those skilled in the art that various changes in form and details may be made therein without departing from the scope of the invention as defined by the appended claims.

What is claimed is:

1. A vortex optical fiber for use in an illumination subsystem of an optical imaging system, the vortex optical fiber comprising an elongated optically transmissive medium having a set of regions including a core region, a trench region surrounding the core region, a ring region surrounding the trench region, and a cladding region, the set of regions having a doping profile providing a $\Delta n_{\textit{eff}}$ for vector modes in an $LP_{11}$ mode group of greater than $1\times10^{-4}$ in the visible spectral range so as to simultaneously guide stable Gaussian and orbital angular momentum (OAM) carrying modes at corresponding visible wavelengths.

2. The vortex optical fiber of claim 1, being either a double-clad or triple-clad design for efficient collection of a backward-propagating optical signal from a sample illuminated by the illumination subsystem.

3. The vortex optical fiber of claim 2, wherein the backward-propagating optical signal is a fluorescence signal and the double-clad or triple-clad design is tailored for collection of the fluorescence signal.

4. The vortex optical fiber of claim 3, wherein the cladding region has a composition that maintains spectral separation between a first signal from fluorescence from dopants and materials of the cladding region and a second signal from fluorescence of the sample, thereby limiting auto-fluorescence.

5. The vortex optical fiber of claim 3, being one of (i) triple clad with low n polymer for guidance of backward propagating fluorescence; (ii) triple clad with air clad for guidance of backward propagating fluorescence; (iii) triple clad with low n glass for guidance of backward propagating fluorescence.

6. The vortex optical fiber of claim 2, wherein a cladding refractive index is effective to establish a numerical aperture of a cladding waveguide larger than 0.4.

7. The vortex optical fiber of claim 1, wherein the doping profile provides for a vortex mode cutoff of greater than 200 nm from an operating wavelength.

8. The vortex optical fiber of claim 7, wherein the higher order modes include $HE_{11}$ and $HE_{21}$.

9. The vortex optical fiber of claim 1, configured to provide an $LP_{01}$ mode having a shape such that an overlap integral with a Gaussian beam is greater than 80%.

10. The vortex optical fiber of claim 1, wherein higher order modes have respective cutoffs within 50 nm of the operating wavelength.

11. The vortex optical fiber of claim 1, wherein the trench region is an inner trench region, and further including an outer trench region effective to reduce bend loss for the vortex modes.

12. The vortex optical fiber of claim 1, including an inscribed optical grating having a grating period between 100 um and 800 um to provide required mode excitation.

13. An illumination subsystem for use in an optical imaging system and employing the vortex optical fiber of claim 1, including one or more mode excitation components providing mode excitation via ultraviolet (UV) or microbend induced, or acousto-optically generated fiber gratings, q-plates, spatial light modulators, metasurfaces and other free-space optical components capable of converting spin to orbital angular momentum of light.

14. The illumination subsystem of claim 13, further including a UV long-period grating for mode conversion.

15. The illumination subsystem of claim 13, further including a chirped grating for broadband mode conversion for ultrafast laser pulses.

16. The illumination subsystem of claim 13, further including an acousto-optically generated fiber grating for tunable optical beam generation over wide spectral bandwidth.

17. The illumination subsystem of claim 13, further including a mechanical microbend grating for mode conversion.

18. The illumination subsystem of claim 13, further including mode stripping tapers at an input end to ensure only $LP_{01}$ mode at all wavelengths go through the core of the vortex optical fiber prior to mode conversion of a depletion optical signal with grating mode converters.

19. The illumination subsystem of claim 13, including free-space devices configured and operative as mode converters for common path mode conversion.

20. The illumination subsystem of claim 19, wherein the mode converters have sufficient chromatic dispersion so only a depletion optical signal is converted into an OAM beam at an input of the vortex optical fiber, while an excitation optical signal remains Gaussian shaped.

21. The illumination subsystem of claim 19, wherein the free-space devices include one or more of q-plates and spatial light modulators.

22. The illumination subsystem of claim 13, including a q-plate with polarization multiplexing and mode/beam cleaning such that an excitation optical signal of circular polarization is combined with a depletion optical signal of an orthogonal polarization before an input of the vortex optical fiber, so that virtually more color pairs of excitation and depletion signals are created using a single q-plate device.

23. The illumination subsystem of claim 13, including respective sources of an excitation optical signal and a depletion optical signal, and wavelength division multiplexers and couplers configured and operative to combine the excitation optical signal and depletion optical signal before an input into the vortex optical fiber.

24. The illumination subsystem of claim 23, forming part of an endoscope having optomechanics to enable scanning a beam from an output of the vortex optical fiber.

25. The illumination subsystem of claim 23, wherein an output of the optical vortex fiber is connected to a microscope arrangement that allows for sample scanning.

26. The illumination subsystem of claim 23, wherein the vortex optical fiber is aligned with microscope elements such that a point spread function remains (1) aligned at a focal plane for the excitation optical signal and depletion optical signal, and (2) aligned in a propagation direction to limit lateral walk-off between the excitation optical signal and the depletion optical signal.

27. The illumination subsystem of claim 23, including use of four wave mixing within OAM modes in the vortex optical fiber to generate the excitation optical signal and depletion optical signal that are naturally temporally synchronized.

28. The illumination subsystem of claim 23, including use of nonlinear frequency generation techniques to simultaneously provide mode conversion as required for the depletion optical signal beam.

29. A confocal stimulated emission depletion (STED) microscopy system employing the vortex optical fiber of claim 1, including respective sources of an excitation optical signal and a depletion optical signal, and wavelength division multiplexers and couplers configured and operative to combine the excitation optical signal and depletion optical signal before an input into the vortex optical fiber.

30. The confocal STED microscopy system of claim 29, wherein the vortex optical fiber is terminated with the standard fiber connectors for incorporating to standard microscope input ports.

31. The confocal STED microscopy system of claim 29, including a coupler that additionally couples and separates cladding modes from core modes, in order to collect backward propagating fluorescence from a sample.

32. The confocal STED microscopy system of claim 29, including a collection of components for fluorescence collection through core modes of the vortex optical fiber, including circulators and beam splitters at a proximal or input end to separate a fluorescence beam from other beams for sending the fluorescence beam to an optical detector.

33. The confocal STED microscopy system of claim 32, wherein a scanned beams fiber output is imaged onto a back-aperture of the high NA lens or onto a scanned sample plane through the high NA objective lens.

34. The confocal STED microscopy system of claim 32, wherein a scanned beams fiber output is coupled to a GRIN lens.

35. The confocal STED microscopy system of claim 29, further including a set of optical components to couple an output of the vortex optical fiber with a high numerical-aperture (NA) objective lens at a sample plane.

36. The confocal STED microscopy system of claim 29, forming part of an endoscope having optomechanics to enable scanning a beam from an output of the vortex optical fiber.

37. The confocal STED microscopy system of claim 36, wherein the optomechanics further provide for collecting a fluorescence signal from the sample.

38. The confocal STED microscopy system of claim 29, wherein an output of the optical vortex fiber is connected to a microscope arrangement that allows for sample scanning.

39. The confocal STED microscopy system of claim 38, wherein the microscope arrangement includes either a sample scanning stage or galvo mirrors for translating optical beams.

40. The confocal STED microscopy system of claim 29, wherein the vortex optical fiber is aligned with microscope elements such that a point spread function remains (1) aligned at a focal plane for the excitation optical signal and depletion optical signal, and (2) aligned in a propagation direction to limit lateral walk-off between the excitation optical signal and the depletion optical signal.

41. The confocal STED microscopy system of claim 29, configured with a system alignment for maximum collection of fluorescence from a sample.

42. The confocal STED microscopy system of claim 29, including time gated fluorescence collection and synchronized excitation and depletion optical signal to maximize depletion after excitation.

43. The confocal STED microscopy system of claim 29, including time gated detection with pulsed excitation sources to minimize influence of fiber auto-fluorescence and unwanted background signal outside the detection time gate.

44. The confocal STED microscopy system of claim 29, including packaged input couplers connecting the sources to the vortex optical fiber and connecting the vortex optical fiber to microscope elements.

45. The confocal STED microscopy system of claim 29, including use of four wave mixing within OAM modes in the vortex optical fiber to generate the excitation optical signal and depletion optical signal that are naturally temporally synchronized.

46. The confocal STED microscopy system of claim 29, including use of nonlinear frequency generation techniques to simultaneously provide mode conversion as required for the depletion optical signal beam.

* * * * *